(12) United States Patent
Priou et al.

(10) Patent No.: US 6,376,721 B1
(45) Date of Patent: Apr. 23, 2002

(54) PROCESS FOR ALKOXYLATION IN THE PRESENCE OF RARE EARTH TRIFLIMIDES

(75) Inventors: Christian B. Priou, West Windsor, NJ (US); Paul-Joel Derian, Villennes-sur Seine; Frédéric Leising, Avilly Saint-Leonard, both of (FR)

(73) Assignee: Rhodia, Inc., Cranbury, NJ (US)

( * ) Notice: Subject to any disclaimer, the term of this patent is extended or adjusted under 35 U.S.C. 154(b) by 0 days.

(21) Appl. No.: 09/765,755

(22) Filed: Jan. 19, 2001

(51) Int. Cl.$^7$ ............................ C07C 43/11; B01J 23/00
(52) U.S. Cl. ...................... 568/618; 568/606; 568/613; 502/303; 502/302; 502/304; 502/162; 502/200
(58) Field of Search ................................ 568/618, 606, 568/613; 502/302, 303, 304, 162, 200

Primary Examiner—Johann Richter
Assistant Examiner—Elvis O. Price

(74) Attorney, Agent, or Firm—Ohlandt, Greeley, Ruggiero & Perle, L.L.P.

(57) ABSTRACT

Disclosed is a process for making alkoxylates of organic compounds. The process requires a) providing an active hydrogen organic compound having 1 to 22 carbon atoms and b) alkoxylating the organic compound with an alkylene oxide in the presence of a catalytically effective amount of a rare earth triflimide of the following formula:

$R^1R^2R^3X$ wherein X is a lanthanide; $R^1$, $R^2$, and $R^3$ each being independently a triflimide group of the following formula:

$N(SO_2Z)_2$ wherein Z is $C_nF_{2n+1}$; C being a carbon atom; F being a fluorine atom; and n being an integer from 1 to 15.

15 Claims, No Drawings

PROCESS FOR ALKOXYLATION IN THE PRESENCE OF RARE EARTH TRIFLIMIDES

BACKGROUND OF THE INVENTION

1. Field of the Invention

The invention relates to a process for making alkoxylates of narrow molecular weight distribution. More particularly, the invention relates to a process for alkoxylation in the presence of a catalyst of rare earth triflimides.

2. Background of the Invention

Nonionic Surfactants are industrially manufactured by reaction of a organic compound with ethylene oxide using a base as catalyst e.g. sodium or potassium hydroxide. Nonionic surfactants are commonly manufactured from the ethoxylation of fatty alcohols.

When a relatively low degree of ethoxylation, i.e. one to four moles, is desired, an undesirably broad molecular weight product distribution is obtained. The broad distribution is due to the similar basicity of the alcohol and ethoxylate. Additive ethoxylation proceeds at the expense of ethoxylation of alcohol. Consequently, low mole ethoxylate products typically have relatively large amounts of unreacted alcohol. Residual alcohol in the product presents odor problems and reduces the smoke point. A low smoke point is especially problematic during the spray-drying of powdered detergents containing ethoxylated nonionic surfactants, when a low smoke point may result in undesirable volatilization of the surfactants.

In addition to higher smoke points and lower odor, ethoxylates of narrow molecular weight distribution have performance advantages over ethoxylates of broad molecular weight distribution. They include the following: (i) lower viscosity and pour point for easier handling; (ii) higher cloud point; (iii) higher initial foaming and less foam stability; (iv) better wetting properties; (v) increased interfacial surface tension reduction compared to paraffin; and (vi) higher surface tension than conventional ethoxylates.

Various processes have been proposed in the base catalysis art to reduce the molecular weight distribution of alkoxylates. Such art is seen, for example, in U.S. Pat. Nos. 3,471,411; 3,969,417; 4,112,231; 4,210,764; 4,223,163; 4,223,164; 4,239,917; 4,278,820; 4,302,613; 4,306,093; 4,360,698; 4,396,779; 4,453,022; 4,465,877; 4,453,023; 4,456,773; 4,456,697; 4,721,817; 4,727,199; 4,754,075; 4,764,567; 4,775,653; 4,885,009; 4,832,321 and 5,220,046, which are incorporated herein by reference. However, the art has to date failed to propose a base catalysis process for making alkoxylates of sufficiently narrow molecular weight distribution.

One means for making alkoxylates of narrower molecular weight distribution is to employ acid catalysis to effect polymerization. Acid catalysis has been generally disfavored, however, in the art because of the formation of relatively high levels of undesirable by-products. For instance, polyoxyethylene is formed by competing dehydration reactions and dioxane and 2-methyldioxolane are formed by competing cyclization reactions.

Processes for making alkoxylates of narrow molecular weight range with catalysts of rare earth metals have been proposed. U.S. Pat. Nos. 5,057,627 and 5,057,628 disclose processes for making alkoxylates of narrow molecular weight range with catalysts of monometallic salts of rare earth elements. U.S. Pat. No. 5,059,719 discloses processes for making alkoxylates with basic rare earth compounds such as rare earth alkoxides. U.S. Pat. No. 5,641,853 discloses the polymerization of oxetanes, 1,3-dioxolanes, 1,3,5-trioxanes and tetrahydrofurans to linear polyethers with metal compounds such as rare earth triflates and perfluoroalkylsulfonates. U.S. Pat. No. 5,677,412 discloses the polymerization of cyclic ethers and organic isocyanates catalyzed by metal compounds such as transition metal and rare earth perfluoroalkylsulfonates and rare earth triflates. EP 855417 discloses a process for making ethoxylates from a hydrogen labile compound and a alkyleneoxide using perfluoroalkylsulfonate salts of transition metals or rare earths. Rare earth triflates are preferred. Rare earth catalysts have afforded the production of ethoxylates of narrower molecular weight distribution with a lower degrees of residual active hydrogen organic starting material, i.e. an alcohol.

In view of the foregoing, it would be desirable to have a new and effective process for making alkoxylates of still narrower molecular weight distribution. Further, it would be desirable to have a process which afforded a still lower degree of residual active hydrogen organic starting material. Still further, it would be desirable to have a process which afforded a lower degree of undesirable by-products.

SUMMARY OF THE INVENTION

It is an object of the present invention to produce alkoxylated organic compounds of narrow molecular weight distribution.

It is a further object of the present invention to produce alkoxylated organic compounds and leave relatively low proportions of residual starting materials.

It is a further object of the present invention to produce alkoxylated organic compounds with relatively low proportions of undesirable by-products.

It is still a further object of the present invention to provide a process for making alkoxylates of active hydrogen organic compounds. The process requires (a) providing an active hydrogen organic compound having an alkyl group of about 8 to about 20 carbon atoms and (b) alkoxylating the organic compound in the presence of a catalytically effective amount of a rare earth triflimide of the following formula:

$$R^1R^2R^3X$$

wherein X is selected from the group of lanthanides, consisting more specifically of neodymium, ytterbium, gadolinium, lanthanum, cerium, praseodymium, samarium, europium, terbium, dysprosium, erbium, thulium, and lutetium. $R^1$, $R^2$, and $R^3$ are each independently a triflimide group of the following formula:

$$N(SO_2Z)_2$$

wherein Z is $C_nF_{2n+1}$. C is a carbon atom and F is a fluorine atom. "n" is an integer from 1 to 15. Z is preferably $CF_3$.

DETAILED DESCRIPTION OF THE INVENTION

In the process of the present invention, it was found unexpected that alkoxylates of narrow molecular weight distribution could be prepared using a catalyst of rare earth triflimides. It was also surprising that such alkoxylates could be prepared leaving a relatively low degrees of residual active hydrogen organic starting material and undesirable by-products.

The rare earth triflimide catalysts useful in the present invention are of the following formula:

$R^1R^2R^3X$ wherein X is selected from the group of lanthanides, consisting more specifically of neodymium, ytterbium, gadolinium, lanthanum, cerium, praseodymium, samarium, europium, terbium, dysprosium, erbium, thulium, and lutetium. $R^1$, $R^2$, and $R^3$ are each independently a triflimide group of the following formula:

$N(SO_2Z)_2$ wherein Z is $C_nF_{2n+1}$. C is a carbon atom and F is a fluorine atom. "n" is an integer from 1 to 15. Z is preferably $CF_3$.

Preferred rare earth triflimides are those of neodymium, ytterbium and gadolinium. Corresponding formulas for the preferred triflimides are $Nd[N(SO_2CF_3)_2]_3$, $Yb[N(SO_2CF_3)_2]_3$ and $Gd[N(SO_2CF_3)_2]_3$.

Rare earth triflimides can be prepared by reaction of rare earth oxides and bistrifluoromethane sulfonamide acid. For instance, the preparation of lanthanum triflimides is shown in the following reactions:

$Ln_2O_3+6(CF_3SO_2)_2NH \rightarrow 2Ln[N(SO_2CF_3)_2]_3+3H_2O$ or $Ln_2(CO_3)_3+6(CF_3SO_2)_2NH \rightarrow 2Ln[N(SO_2CF_3)_2]_3+3CO2$ The rare earth triflimide catalyst is employed in a catalytically effective amount. Preferably, the catalysts are employed at about $1.0 \times 10^{-5}$ M to about $1.0 \times 10^{-1}$ M based on the organic compound.

The active hydrogen organic compound employed in the present process has 1 to 22 carbon atoms. Useful active hydrogen organic compounds include alcohols, amines, mercaptans and amides. Preferred compounds are hydrophobic and have from 8 to 22 carbon atoms. Preferred compounds are also hydroxylated. Preferred compounds include fatty alcohols. Fatty alcohols can be obtained from natural sources such as fats and oils or may be derived synthetically from petroleum. Natural alcohols are prepared from natural fatty acids derived from coconut oil, palm kernel oil, palm oil, tallow, soya, sperm oils and the like. Useful fatty alcohols include octanol, nonanol, decanol, dodecanol, palmityl alcohol, octadecanol, eicosanol, behenyl alcohol, and stearyl alcohol and mixtures or blends of the foregoing. A most preferred fatty alcohol is dodecanol. Unsaturated alcohols such as oleoyl, linoleic and linolenic alcohols are also useful. Synthetic alcohols may be prepared using the oxo (hydroformylation of carbon monoxide and hydrogen) or the Ziegler (ethylene and triethylaluminum) processes. Typical alcohols are oxodecyl, oxotridecyl, oxotetradecyl alcohol. Useful alcohols include Neodol 23, 25 and 91 (Shell Corp.). Aromatic alcohols are also useful. Typical aromatic alcohols are nonylphenol, octylphenol, diisobutylphenol, dodecylphenol and dinonylphenol. Useful low molecular weight alcohols include methanol, ethanol, propanol, butanol and other $C_1$ to $C_7$ alcohols.

Alkoxylation is carried out by contacting the active hydrogen organic compound with an alkylene oxide under catalytically effective conditions. The reaction is carried out in the presence of the rare earth triflimides, which are Lewis acids. The alkoxylation reaction can be carried out in temperature conditions from about 20° C. to 200° C.

Alkoxylation include the reactions of ethoxylation, propoxylation, and butoxylation. Alkoxylation reactions involving adducts of higher numbers of carbons are possible and within the scope of the invention. Useful alkylene oxide reactants include but are not limited to ethylene oxide, propylene oxide, butylene oxide and cyclohexene oxide. An important reaction industrially is ethoxylation, which typically involves the addition of ethylene oxide to a organic compound. More specifically, an important reaction is the ethoxylation of dodecanol.

The present process affords the production of product having relatively narrow molecular weight distribution. Although not bound by any particular range or level of distribution, degrees of narrowing up to about 95% are possible. Preferred degrees of narrowing range from about 80 to about 95%. Degree of narrowing are determined according to the formula and method set forth below.

The present process affords advantages over conventional base catalysis of the prior art. The present process yields alkoxylated product of considerably narrower molecular weight distribution than that produced by conventional base catalysis using potassium or sodium hydroxide. Further, the present process leaves a lower residual content of active hydrogen organic starting material, i.e. fatty alcohols, than conventional base catalysis. Further, the present process can be effected at a lower operating temperatures than with conventional base catalysis. Still further, the present process can be effected with about a tenth of the amount of catalyst normally employed in conventional base catalysis.

The catalyst can be used as is or can be supported on a mineral charge such as silica, alumno, titanium dioxide and the like. The catalyst can be left in the final product or be recycled after proper treatment.

The following are non-limiting examples of the present invention. All percentages are by weight unless indicated otherwise.

EXAMPLES

Ethoxylates were prepared according to the process of the present invention via catalysis with rare earth triflimides. The relative degrees of narrowing, residual starting material content, and by-product content were measured. The results were compared to ethoxylates prepared via conventional base catalysis.

The degree of narrowing was defined according to the following formula:

$$\text{Degree of Narrowing } DN = \sum_{n=n\,\text{max}-2}^{n=n\,\text{max}-2} Yi$$

wherein n max=the molar number of added ethylene oxide (or alkylene oxide) in an adduct accounting for a maximum proportion by weight in a total adduct.

Yi=proportion by weight of an adduct having "i" moles of added ethylene oxide to a total weight of the adduct.

For degree of narrowing determinations, the gas chromatographic (GC) area % was used. The degree of narrowing is expressed as a percentage (%). The higher the percentage, the narrower the molecular weight distribution. The formula and method are set forth in *Narrow Alcohol Ethoxylates,* Annual Surfactants Reviews, vol. 2, Ed. D. R. Karsa (1999).

In the Examples herein, gadolinium triflimide was prepared according to the following: (1) $2.24 \times 10^{-3}$ moles of $Gd_2O_3$ in 5 ml of deionized water is charged into a round bottom flask equipped with a condenser; (2) 34 ml of 0.39

M aqueous solution of bistrifluoromethane sulfonamide acid acid is added; (3) the mixture is brought to reflux over one hour; (4) then the mixture is cooled to room temperature and filtered to eliminate excess oxide; (5) water is evaporated; (6) 20 ml of ethanol is added and then evaporated; (7) the above step is repeated twice (three addition/evaporation steps total). Drying (evaporation) is performed under vacuum over 24 hours at 72 millibars pressure at 70° C. The resulting powder is used as soon as possible after drying, preferably under inert atmosphere, or stored under inert atmosphere.

Neodymium triflimide is prepared in the same manner as for gadolinium triflimide except that $Nd_2O_3$ was substituted for $Gd_2O_3$. In addition, the neodymium triflimide is not dried.

Comparative Example (R-111-132)

In this comparative example, ethylene oxide was reacted with dodecanol on a 3:1 mole basis in the presence of a potassium hydroxide catalyst. Dodecanol (Aldrich, 98%+ Reagent) at 199.7 grams (gm) (1.07 moles) and potassium hydroxide at 3.56 gm (45%, 1.6 gm of 100%) of were charged to a two liter autoclave. The autoclave was heated with nitrogen sparge to 120° C. The autoclave was vacuum stripped for one hour with a slight nitrogen sparge. The vacuum was secured, then the reactor was pressurized to 20 psi with nitrogen and heated to 150° C. Ethylene oxide (141.5 gm) was added to the reactor over a one hour period at 150° C. and 50 pounds per square inch gauge (psig) and held for an additional hour. The reactor was cooled to 120 ° C. and vacuum stripped for 10 minutes. The reactor was then cooled further and 321 gm of product discharged. Reaction conditions and results are set forth in the Table.

Example 1 (R-111-129)

In this example, ethylene oxide was reacted with dodecanol on a 3:1 mole basis in the presence of a neodymium triflimide catalyst. Dodecanol (Aldrich) at 200.1 gm (1.08 moles) and containing $2.89 \times 10^{-3}$ M of neodymium triflimide was charged to a 2 liter autoclave. The reactor was heated to 110° C. with a nitrogen sparge. The reactor was vacuum stripped for one (1) hour at 110° C. with a slight nitrogen bleed. The reactor was then pressurized to 20 psig with nitrogen and 140.5 gm (3.22 M) of ethylene oxide was added over three hours and ten minutes at 50 psig. The reactor was stripped at 110° C. for fifteen minutes at a 3–4 psig vacuum. The reactor was cooled to room temperature and 300 gm of product was discharged.

Reaction conditions and results are set forth in the Table. The ethoxylate product exhibited a higher degree of narrowing (92% versus 62.5%) and a lower residual alcohol content (1.6% versus 12.6%) than the Comparative Example.

Example 2 (R-111-142)

Example 2 was carried out in the same manner as for Example 1. Three moles of ethylene oxide were added per mole of dodecanol. In Example 2, 10% molar of di-ter-butylpyridine (DBTP) was added as a proton trap. Results are set forth in the Table.

The ethoxylated product of Example 2 exhibited a higher degree of narrowing and a lower amount of residual dodecanol than the Comparative Example.

Example 3 (R-111-95) and Example 4 (R-111-98)

Examples 3 and 4 were carried out in the same manner as for Example 1. Gadolinium triflimide was employed in Example 3 and neodymium triflimide was employed in Example 4. Seven moles of ethylene oxide were added per mole of dodecanol. Results are set forth in the Table.

The ethoxylated products of both Examples 3 and 4 both exhibited higher degrees of narrowing and lower amounts of residual dodecanol than the Comparative Example.

TABLE

| Reference | Catalyst | Catalyst Amount (mole %) in dodecanol | Reaction Time | Color | Degree Of Narrowing (%) | Dioxane (wt. %) | Dodecanol (wt. %) | PEG (wt. %) |
|---|---|---|---|---|---|---|---|---|
| R-111-132* | KOH | 2.64 | 52 minutes | pale yellow | 62.5 | 0.0018 | 12.6 | 1.7 |
| R-111-129 | $Nd(TfSi)_3$ | 0.264 | 3 hours | colorless | 91 | 0.3 | 1.6 | 0.8 |
| R-111-142 | $Nd(TfSi)_3$ + DTBP | 0.264 | 3 hours | yellow | 92 | 0.4 | 1.7 | 1 |
| R-111-95 | $Gd(TfSi)_3$ | 0.264 | 3 hours | Light brown | 83.5 | 1.6 | 0.12 | 7.1 |
| R-111-98 | $Nd(TfSi)_3$ | 0.264 | 3 hours | Light brown | 84 | 1.6 | 0.08 | 7 |

*Not an example of the present invention

It should be understood that the foregoing description is only illustrative of the present invention. Various alternatives and modifications can be devised by those skilled in the art without departing from the invention. Accordingly, the present invention is intended to embrace all such alternatives, modifications and variances which fall within the scope of the appended claims.

What is claimed is:

1. A process for making alkoxylates of organic compounds, comprising:
   a) providing an active hydrogen organic compound having 1 to 22 carbon atoms and
   b) alkoxylating the active hydrogen organic compound with an alkylene oxide in the presence of a catalytically effective amount of a rare earth triflimide of the following formula:

$R^1R^2R^3X$ wherein X is a lanthanide; $R^1$, $R^2$, and $R^3$ each being independently a triflimide group of the following formula:

$N(SO_2Z)_2$ wherein Z is $C_nF_{2n+1}$; C being a carbon atom; F being a fluorine atom; and n being an integer from 1 to 15.

2. The process of claim 1, wherein the lanthanide is selected from the group consisting of neodymium, ytterbium, gadolinium, lanthanum, cerium, praseodymium, samarium, europium, terbium, dysprosium, erbium, thulium, and lutetium.

3. The process of claim 1, wherein the Z is $CF_3$.

4. The process of claim 1, wherein the rare earth triflimide is selected from the group consisting of gadolinium triflimide, neodymium triflimide, ytterbium triflimide.

5. The process of claim 1, wherein the active hydrogen compound is selected from the group consisting of alcohols, amines, mercaptans and amides.

6. The process of claim 5, wherein the organic compound is a fatty alcohol having from 8 to 22 carbon atoms.

7. The process of claim 6, wherein the fatty alcohol is dodecanol.

8. The process of claim 1, wherein the catalyst is present at about $1.0 \times 10^{-5}$ M to about $1.0 \times 10^{-1}$ M based on the organic compound.

9. The process of claim 1, wherein the alkoxylation is carried out at from about 20° C. to 170° C.

10. The process of claim 1, wherein the alkylene oxide is ethylene oxide.

11. The process of claim 1, wherein 1 to 100 moles of alkylene oxide per mole of organic compound are reacted during alkoxylation.

12. The process of claim 1, wherein 2 to 4 moles of alkylene oxide per mole of organic compound are reacted during alkoxylation.

13. The process of claim 1, wherein the rare earth triflimide is selected from the group consisting of gadolinium triflimide, neodymium triflimide, ytterbium triflimide, the active hydrogen organic compound being a fatty alcohol having from 8 to 22 carbon atoms, the alkylene oxide being ethylene oxide the catalyst being present at about $1.0 \times 10^{-5}$ M to about $1.0 \times 10^{-1}$ M based on the active hydrogen organic compound, the alkoxylation being carried out at from about 20° C. to 170° C., 1 to 100 moles of alkylene oxide per mole of fatty alcohol are reacted during alkoxylation.

14. The process of claim 13, wherein the fatty alcohol is dodecanol.

15. The process of claim 14, wherein 2 to 4 moles of alkylene oxide per mole of fatty alcohol are reacted during alkoxylation.

* * * * *